(12) United States Patent
Pystynen et al.

(10) Patent No.: US 6,951,870 B2
(45) Date of Patent: Oct. 4, 2005

(54) COUMARIN DERIVATIVES WITH COMT INHIBITING ACTIVITY

(75) Inventors: Jarmo Pystynen, Espoo (FI); Martti Ovaska, Espoo (FI); Jukka Vidgren, Siuntio (FI); Timo Lotta, Vantaa (FI); Marjo Yliperttula-Ikonen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 10/312,817

(22) PCT Filed: Jun. 28, 2001

(86) PCT No.: PCT/FI01/00613

§ 371 (c)(1),
(2), (4) Date: Mar. 31, 2003

(87) PCT Pub. No.: WO02/02548

PCT Pub. Date: Jan. 10, 2002

(65) Prior Publication Data

US 2004/0110750 A9 Jun. 10, 2004

(30) Foreign Application Priority Data

Jul. 3, 2000 (FI) .............................................. 20001593

(51) Int. Cl.[7] ........................ A61K 31/35; A61K 31/47; C07D 307/93; C07D 215/16; C07D 215/36
(52) U.S. Cl. ....................... 514/312; 514/313; 514/314; 514/456; 546/153; 546/155; 546/156; 546/157; 546/159; 546/164; 549/466; 549/467; 549/468
(58) Field of Search ................................ 549/466, 467, 549/468, 461; 546/153, 155, 156, 157, 159, 164; 514/312, 313, 314, 456

(56) References Cited

U.S. PATENT DOCUMENTS

| | | | |
|---|---|---|---|
| 3,973,608 A | 8/1976 | Umezawa et al. | |
| 5,019,570 A | 5/1991 | Arnould et al. | |
| 5,650,439 A | 7/1997 | Nakamura et al. | |

FOREIGN PATENT DOCUMENTS

| | | |
|---|---|---|
| WO | WO 93/16064 | 8/1993 |
| WO | WO 98/27973 | 7/1998 |

OTHER PUBLICATIONS

Ericsson, A.D., "Potentiation of the L–Dopa Effect in Man by the Use of Catechol–O–Methyltransferase Inhibitors," Journal of the Neurological Sciences, vol. 14, pp. 193–197 (1971).

C.E. Cook et al., "Flavonoids. I. Synthesis of 2,2–Dialkyl–$\Delta^3$–isoflavenes from Coumarins[1]", J. Org. Chem., vol. 30, pp. 4114–4122 (1965).

C.E. Cook et al., "Flavonoids. II. Rearrangement of 2,2–Dimethyl–$\Delta^3$–isoflavenes to Indenes[1]", J. Org. Chem., vol. 30, pp. 4120–4122 (1965).

Timo Lotta et al., "Kinetics of Human Soluble and Membrane–Bound Catechol O–Methyltransferase: A Revised Mechanism and Description of the Thermolabile Variant of the Enzyme", J. Biochemistry, vol. 34, pp. 4202–4210 (1995).

B.S. Bajwa et al., "Nuclear Prenylation of Polyhydroxyacetophenones in Aqueous Acid Medium", Indian Journal of Chemistry, vol. 11, pp. 100–103 (1973).

*Primary Examiner*—Cecilia J. Tsang
*Assistant Examiner*—Raymond Covington
(74) *Attorney, Agent, or Firm*—Finnegan, Henderson, Farabow, Garrett & Dunner, LLP

(57) ABSTRACT

Compounds of formula I'

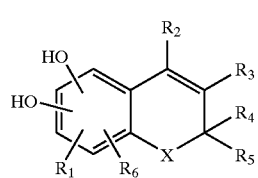

wherein the two —OH substituents in the phenyl moiety are in a position ortho to one another and $R_1$ in a position ortho to one of the hydroxy groups; and X, $R_1$ to $R_6$ are as defined in disclosure. The compounds exhibit COMT enzyme inhibiting activity, so are useful as COMT inhibitors.

15 Claims, No Drawings

COUMARIN DERIVATIVES WITH COMT INHIBITING ACTIVITY

This application is a national stage filing of PCT International Application No. PCT/FI01/00613, filed on Jun. 28, 2001. This application also claims the benefit of priority under 35 U.S.C. § 119(a) to Finnish patent application no. 20001593, filed on Jul. 3, 2000.

FIELD OF THE INVENTION

The present invention relates to coumarin derivatives and pharmaceutically acceptable salts and esters thereof. The invention further relates to pharmaceutical compositions thereof and to their use as inhibitors of catechol-O-methyltransferase (COMT) enzyme.

BRIEF DESCRIPTION OF THE PRIOR ART

Compounds with COMT inhibiting activity are already known. For example, derivatives of catechols and isoflavones as COMT inhibitors have been disclosed i.a. in U.S. Pat. No. 5,446,194, U.S. Pat. No. 5,389,653 and, respectively, in U.S. Pat. No. 3,973,608. COMT inhibitors are used i.a. in the treatment of Parkinson's disease. COMT-inhibitors have also indicated to be useful in the treatment of i.a. hypertension, heart failure and depression (cf. e.g. U.S. Pat. No. 446,194 above) as well as inhibitors for the prevention of diabetic vascular dysfunctions (cf. WO-A-98 27973).

As to the known derivatives of coumarin, WO-A-93 16064 discloses coumarins with tyrosine kinase enzyme inhibiting activity to be used as antitumor agents. Furthermore, J.Mazur and T.Zawadowski (Acta Pol.Pharm., vol.54(5), 1997, p.371–374, see also Pol.J.Chem., vol.55(5), 1981, p.1151–5), D.Desai and R. H. Mehta (Indian J.Heterocycl.Chem., vol.6(3), 1997, p.241–244) and A. C. Jain et al. (Bull.Chem.Soc.Jpn, vol.52(4), 1979, p.1203–4) describe various coumarin derivatives with i.a. antibacteric, hypotensive, spasmolytic and/or antileukaemic activity.

SUMMARY OF THE INVENTION

The object of the present invention is to provide further compounds with catechol-O-methyltransferase enzyme inhibiting activity.

The invention also provides compounds for the treatment of disorders or conditions wherein inhibition of COMT is indicated to be useful, as well as a use thereof for the manufacture of a medicament to be used as a COMT inhibiting agent. Furthermore, pharmaceutical compositions containing the present compounds are provided.

DETAILED DESCRIPTION OF THE INVENTION

The invention thus provides compounds of the general formula I':

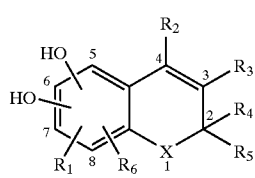

I' wherein the two OH— substituents in the phenyl moiety are in a position ortho to one another and R1 in a position ortho to one of the hydroxy groups;

X is O or $NR_7$; wherein $R_7$ is H, $(C_1-C_6)$alkyl or —$(C_1-C_6)$alkyl-COOH;

$R_1$ is $NO_2$, CN, CHO, $CF_3$ or $(C_1-C_6)$alkyl-CO—;

$R_2$ and $R_3$ are each selected independently from H, OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, mono- or di$(C_1-C_6)$alkylamino, $SO_2R_{10}$, —CO—$(C_1-C_9)$alkyl, —$(Y)_n$—$(B)_m$—COOH and —$(Y)_n$—$(B)_m$—$R_8$; wherein m is 0 or 1;
n is 0 or 1;
Y is —CO— or —CHOH—;
B is $(C_1-C_6)$alkylene or $(C_2-C_6)$alkenylene;
$R_8$ is phenyl, naphthyl, $(C_3-C_7)$cycloalkyl or 5- or 6-membered heterocyclyl with one to four heteroatoms each selected independently from N, O and S, wherein the said phenyl, naphthyl, $(C_3-C_7)$cycloalkyl or 5- or 6-membered heterocyclyl is optionally substituted with one to five substituents $R_9$ each selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH and $SO_2R_{10}$;

or $R_8$ is

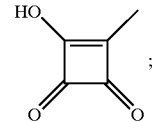

or $R_2$ and $R_3$ form together —$(CH_2)_r$—; wherein r is 3, 4 or 5;

$R_4$ and $R_5$ are independently H or $(C_1-C_6)$alkyl; or $R_4$ and $R_5$ form together =O, =S or =$NR_{11}$, wherein $R_{11}$ is H or $(C_1-C_6)$alkyl;

$R_6$ is H, $NO_2$, CN, CHO, halogen, $CF_3$ or $(C_1-C_6)$alkyl; and $R_{10}$ is $(C_1-C_6)$alkyl, $NH_2$, OH or mono- or di$(C_1-C_6)$alkylamino;

or pharmaceutically acceptable salts or pharmaceutically acceptable esters thereof.

As a subgroup of the compounds I' the invention provides new compounds of formula I,

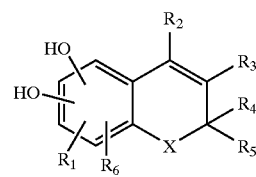

I wherein X, $R_1$ to $R_6$ are as defined above under the compounds of formula I', with the provisos that (a) when X is O, $R_2$ is methyl, $R_3$ is H, $R_4$ and $R_5$ form together =O, $R_6$ is H and the two hydroxy substituents are at 7- and 8-positions, then $R_1$ is not CHO, (b) when X is O, $R_2$ is H or methyl, $R_3$ is H, $R_4$ and $R_5$ form together =O, $R_6$ is H and the two hydroxy substituents are at 6- and 7-positions, then $R_1$ is not 8-CO—$CH_3$, (c) when X is O, $R_2$ and $R_3$ are H, $R_4$ and $R_5$ are both methyl, $R_6$ is H and the two hydroxy substituents are at 7- and 8-positions, then $R_1$ is not —CO—$CH_3$, or pharmaceutically acceptable salts or pharmaceutically acceptable esters thereof.

The compounds of formula I' and I exhibit COMT inhibiting activity and can thus be used as therapeuticals for the treatment of diseases or conditions wherein COMT inhibitors are indicated to be useful, e.g. for the treatment of Parkinson's disease.

The following subgroups (1) to (15) of compounds of formula I' or I taken alone or in any combination with each other are preferable, (1) $R_1$ is $NO_2$, CN, or $CF_3$, e.g. $NO_2$ or CN, such as $NO_2$;

(2) X is O;

(3) X is $NR_7$; $R_7$ is H or $(C_1-C_6)$alkyl, e.g. H;

(4) $R_2$ and $R_3$ are each selected independently from H, OH, halogen, $NO_2$, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, mono- or di$(C_1-C_6)$alkylamino, —CO—$(C_1-C_9)$alkyl, e.g. —CO—$(C_1-C_6)$alkyl, —$(Y)_n$—$(B)_m$—COOH, e.g. —$(B)_m$—COOH and —Y—B—COOH, and —$(Y)_n$—$(B)_m$—$R_8$; wherein n is 0 or 1; m is 0 or 1; Y is —CO— or —CHOH—, e.g. —CO—; B is $(C_1-C_6)$alkylene or $(C_2-C_6)$alkenylene, e.g. $(C_1-C_6)$alkylene; $R_8$ is phenyl, naphthyl, $(C_3-C_7)$cycloalkyl or 5- or 6-membered heterocyclyl with one to four heteroatoms each selected independently from N, O and S, e.g. phenyl, $(C_3-C_7)$cycloalkyl or 5- or 6-membered heterocyclic ring with one to four heteroatoms each selected independently from N, O and S (e.g. piperidyl, piperazinyl, morpholinyl, tetrazolyl, thienyl, furyl or pyridyl, e.g tetrazolyl or pyridyl) each of which is optionally substituted with one to five, e.g. one to three, such as one or two, e.g. one, substituent(s) $R_9$ each selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, —CO—$(C_1-C_6)$alkyl, —CO—$NH_2$, mono- or di$(C_1-C_6)$alkylamino-CO—, —NHOH, —CONHOH and $SO_2R_{10}$, wherein $R_{10}$ is as defined above (e.g.$(C_1-C_6)$alkyl, $NH_2$ or OH), e.g. from OH, halogen, COOH, 5-tetrazolyl, $NO_2$, $NH_2$, CN, CHO, $(C_1-C_6)$alkyl, $(C_1-C_6)$alkoxy, halo-$(C_1-C_6)$alkyl, mono- or di$(C_1-C_6)$alkylamino, —CO—$(C_1-C_6)$alkyl, —CO—$NH_2$, mono- or di$(C_1-C_6)$alkylamino-CO—, —NHOH and —CONHOH; such as from OH, halogen, COOH, 5-tetrazolyl, $NO_2$, $(C_1-C_6)$alkyl, $(C_1-C_6)$alkoxy and halo-$(C_1-C_6)$alkyl; e.g. from OH, halogen, COOH, 5-tetrazolyl, $NO_2$ and $(C_1-C_6)$alkyl;

(5) $R_2$ and $R_3$ are each selected independently from H, —CO—$(C_1-C_9)$alkyl, —$(Y)_n$—$(B)_m$—COOH, e.g. —$(B)_m$—COOH and —Y—B—COOH, and —$(Y)_n$—$(B)_m$—$R_8$; wherein n is 0 or 1; m is 0 or 1; Y is —CO— or —CHOH—, e.g. —CO—; B is $(C_1-C_6)$alkylene or $(C_2-C_6)$alkenylene, e.g. $(C_1-C_6)$alkylene; $R_8$ is phenyl, naphthyl, $(C_3-C_7)$cycloalkyl or 5- or 6-membered heterocyclic ring with one to four heteroatoms each selected independently from N, O and S, e.g. phenyl, $(C_3-C_7)$cycloalkyl or 5- or 6-membered heterocyclic ring with one to four heteroatoms each selected independently from N, O and S (e.g. piperidyl, piperazinyl, morpholinyl, tetrazolyl, thienyl, furyl or pyridyl, e.g. tetrazolyl or pyridyl) each of which is unsubstituted or substituted with one to five, e.g. one to three, such as one or two, e.g. one, substituent(s) $R_9$ each selected independently from OH, halogen, COOH, 5-tetrazolyl, NHOH, CONHOH, $NO_2$, SH, $NH_2$, CN, CHO, =O, $(C_1-C_6)$alkyl, $(C_1-C_6)$alkoxy and halo-$(C_1-C_6)$alkyl, e.g. $CF_3$, or $R_8$ is

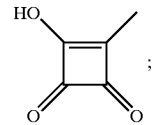

(6) one of $R_2$ and $R_3$ is selected from —CO—$(C_1-C_9)$alkyl, —$(Y)_n$—$(B)_m$—COOH, e.g. —$(B)_m$—COOH and —Y—B—COOH, and —$(Y)_n$—$(B)_m$—$R_8$; wherein n is 0 or 1; m is 0 or 1; Y is —CO— or —CHOH—, e.g. —CO—; B is $(C_1-C_6)$alkylene or $(C_2-C_6)$alkenylene, e.g. $(C_1-C_6)$alkylene; $R_8$ is phenyl, naphthyl, $(C_3-C_7)$cycloalkyl or 5- or 6-membered heterocyclic ring with one to four heteroatoms each selected independently from N, O and S, e.g. phenyl, $(C_3-C_7)$cycloalkyl or 5- or 6-membered heterocyclic ring with one to four heteroatoms each selected independently from N, O and S (e.g. piperidyl, piperazinyl, morpholinyl, tetrazolyl, thienyl, furyl or pyridyl, e.g. 5-tetrazolyl or pyridyl) each of which is unsubstituted or substituted with one to five, e.g. one to three, such as one or two, e.g. one, substituent(s) $R_9$ each selected independently from OH, halogen, COOH, 5-tetrazolyl, NHOH, CONHOH, $NO_2$, SH, $NH_2$, CN, CHO, =O, $(C_1-C_6)$alkyl, $(C_1-C_6)$alkoxy and halo-$(C_1-C_6)$alkyl (e.g. $CF_3$), e.g. from COOH, 5-tetrazolyl, NHOH and CONHOH, e.g. from COOH and 5-tetrazolyl; or $R_8$ is

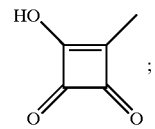

(7) one of $R_2$ and $R_3$ is selected from H, OH, halogen, $NO_2$, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, mono- or di$(C_1-C_6)$alkylamino, —CO—$(C_1-C_9)$alkyl and —$(Y)_n$—$(B)_m$—$R_8$; e.g one of $R_2$ and $R_3$ is —$(Y)_n$—$(B)_m$—$R_8$, wherein n is 0 or 1; m is 0 or 1; Y is —CO— or —CHOH—, e.g. —CO—; B is $(C_1-C_6)$alkylene or $(C_2-C_6)$alkenylene, e.g. $(C_1-C_6)$alkylene; $R_8$ is phenyl, naphthyl, $(C_3-C_7)$cycloalkyl or 5- or 6-membered heterocyclic ring with one to four heteroatoms each selected independently from N, O and S, e.g. phenyl, $(C_3-C_7)$cycloalkyl or 5- or 6-membered heterocyclic ring with one to four heteroatoms each selected independently from N, O and S (e.g. piperidyl, piperazinyl, morpholinyl, tetrazolyl, thienyl, furyl or pyridyl, suitably 5-tetrazolyl or pyridyl) each of which is unsubstituted or substituted with one to five, e.g. one to three, such as one or two, e.g. one, substituent(s) $R_9$ each selected independently from OH, halogen, COOH, 5-tetrazolyl, $NO_2$, SH, $NH_2$, CN, CHO, =O, $(C_1-C_6)$alkyl, $(C_1-C_6)$alkoxy and halo-$(C_1-C_6)$alkyl (e.g. $CF_3$), e.g. from OH, halogen, $NO_2$, CN, CHO, $(C_1-C_6)$alkyl, $(C_1-C_6)$alkoxy and halo-$(C_1-C_6)$alkyl(e.g. $CF_3$); such as from halogen, $NO_2$, $(C_1-C_6)$alkyl and $(C_1-C_6)$alkoxy;

(8) $R_2$ is selected from (7) above;

(9) one of $R_2$ and $R_3$, e.g. $R_3$, is —CO—$(C_1-C_9)$alkyl, —$(Y)_n$—$(B)_m$—COOH, e.g. —$(B)_m$—COOH or —Y—B—COOH, or —$(Y)_n$—$(B)_m$—$R_8$, such as —$(B)_m$—COOH, —Y—B—COOH or —$(Y)_n$—

$(B)_m$—$R_8$, wherein n is 0 or 1; Y is CO; m is 0 or 1, B is $(C_1-C_6)$alkylene, e.g. —$CH_2$—; and $R_8$ is phenyl unsubstituted or substituted with COOH or tetrazol; or $R_8$ is tetrazol, e.g. 5-tetrazol, or pyridyl.

(10) Y is CO;

(11) B is $(C_1-C_6)$alkylene;

(12) one of $R_2$ and $R_3$ is as defined in any of (4) to (7) and/or (9) above and the other of $R_2$ and $R_3$ is selected independently from H, OH, halogen, $NO_2$, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl and mono- or di$(C_1-C_6)$alkylamino; e.g. H, OH, $(C_1-C_6)$alkyl and $(C_1-C_6)$alkoxy; e.g. H, OH and $(C_1-C_6)$alkyl;

(13) $R_2$ and $R_3$ form together —$(CH_2)_r$—, r is 3, 4 or 5, e.g. 3 or 4;

(14) $R_6$ is H, $NO_2$, CHO, halogen, $CF_3$ or $(C_1-C_6)$alkyl (e.g. methyl); such as H, $NO_2$, CHO or $(C_1-C_6)$alkyl (e.g. methyl); e.g. H; and/or

(15) $R_4$ and $R_5$ are independently H or $(C_1-C_6)$alkyl; e.g. $R_4$ and $R_5$ are both methyl; or $R_4$ and $R_5$ form together =O, =S or =NH; e.g. =O or =NH; such as =O.

A subgroup of the compounds of formula I' or I are the compounds of formula Ia,

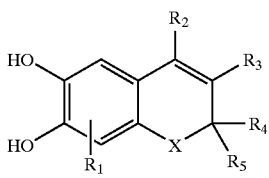

Ia wherein X, $R_1$ to $R_5$ are as defined above.

A further subgroup of the compounds of formula I' or I are the compounds of formula Ib,

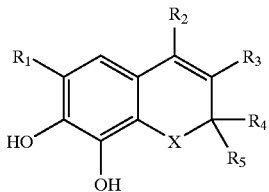

Ib wherein X, $R_1$ to $R_5$ are as defined above.

In a further subgroup of compounds of formula I', I, Ia or Ib, $R_1$ is $NO_2$ or CN, e.g. $NO_2$, and one of $R_2$ and $R_3$, e.g. $R_3$, is —$(Y)_n$—$(B)_m$—COOH, e.g. —$(B)_m$—COOH or —Y—B—COOH, or —$(Y)_n$—$(B)_m$—$R_8$. In another subgroup of compounds I', I, Ia or Ib one of $R_2$ and $R_3$, e.g. $R_3$, is —$(B)_m$—COOH, —Y—B—COOH or —$(Y)_n$—$(B)_m$—$R_8$, n is 0 or 1, Y is CO; m is 0 or 1; B is $(C_1-C_6)$alkylene; $R_8$ is 5-tetrazolyl, or $R_8$ is phenyl or pyridyl unsubstituted or substituted with one or two, e.g. one, substituent(s) selected independently from OH, halogen, $NO_2$, $(C_1-C_6)$alkyl, $(C_1-C_6)$alkoxy, COOH and 5-tetrazolyl. In another subgroup of compounds I', I, Ia or Ib one of $R_2$ and $R_3$, e.g. $R_3$, is —CO—$(C_1-C_9)$alkyl, —$(Y)_n$—$(B)_m$—COOH, e.g. —$(B)_m$—COOH or —Y—B—COOH, or —$(Y)_n$—$(B)_m$—$R_8$.

In another subgroup of the compounds I', I, Ia or Ib, one of $R_2$ and $R_3$ is H, $(C_1-C_6)$alkyl, $(C_2-C_6)$alkenyl, $(C_1-C_6)$alkoxy, —CO—$(C_1-C_9)$alkyl or —$(Y)_n$—$(B)_m$—$R_8$, wherein n, m Y and $R_8$ are as defined above; and the other of $R_2$ and $R_3$ is —CO—$(C_1-C_9)$alkyl, —$(Y)_n$—$(B)_m$—COOH, e.g. —$(B)_m$—COOH or —Y—B—COOH, or —$(Y)_n$—$(B)_m$—$R_8$ as defined above. For example one of $R_2$ and $R_3$, is H or $(C_1-C_6)$alkyl; and the other of $R_2$ and $R_3$, e.g. $R_3$, is —$(B)_m$—COOH, —Y—B—COOH or —$(Y)_n$—$(B)_m$—$R_8$ as defined above, e.g. —$(B)_m$—COOH or —$(Y)_n$—$(B)_m$—$R_8$, e.g. $(C_1-C_6)$alkylene-COOH or —$(Y)_n$—$R_8$, Y is CO, $R_8$ is phenyl or pyridyl unsubstituted or substituted with one or two, e.g. one, substituent(s) selected independently from OH, halogen, $NO_2$, $(C_1-C_6)$alkyl, $(C_1-C_6)$alkoxy, COOH and 5-tetrazolyl, e.g. from OH, halogen, $NO_2$, $(C_1-C_6)$alkyl or $(C_1-C_6)$alkoxy; or $R_8$ is tetrazolyl, e.g. 5-tetrazolyl.

In a further subgroup of the compounds I', I, Ia or Ib, $R_2$ and $R_3$ form together —$(CH_2)_r$—, r is 3 or 4, e.g. 4. Furthermore, preferably in the compounds of formula I', I, Ia or Ib, $R_4$ and $R_5$ form together =O or =NH, e.g. =O, or $R_4$ and $R_5$ are both $(C_1-C_6)$alkyl, e.g. methyl.

In a preferred subgroup of the compounds of formula I' or I, the two hydroxy substitutents at the phenyl ring are in 6- and 7-positions. Preferably, one of $R_2$ and $R_3$ is not H.

The compounds of formula I' and the subgroups I, Ia and Ib, as well as the pharmaceutically acceptable salts and the pharmaceutically acceptable esters thereof, are referred to below as the compounds of the invention, unless otherwise indicated.

The compounds of the invention may have chiral carbon atom(s) in their structure. The invention includes within its scope all the possible stereoisomers of the compounds I, including geometric isomers, e.g. Z and E isomers (cis and trans isomers), and optical isomers, e.g. diastereomers and enantiomers. Furthermore, the invention includes in its scope both the individual isomers and any mixtures thereof, e.g. racemic mixtures. The individual isomers may be obtained using the corresponding isomeric forms of the starting material or they may be separated after the preparation of the end compound according to conventional separation methods. For the separation of i.a. optical isomers, e.g. enantiomers, from the mixture thereof the conventional resolution methods, e.g. fractional crystallisation, may be used.

Physiologically acceptable salts may be prepared by known methods. The pharmaceutically acceptable salts are the usual organic and inorganic salts in the art. Furthermore, the COOH—, OH— and/or amino-functionality, such as COOH— and/or OH— functionality, e.g. COOH— functionality, when present in the compounds of the invention, can be converted to a pharmaceutically acceptable ester or, respectively, a pharmaceutically acceptable amide in a manner known in the art using a pharmaceutically acceptable acid or, respectively, a pharmaceutically acceptable alcohol known from the literature. Examples of such pharmaceutically acceptable acids and alcohols are e.g. aliphatic (e.g. $C_1-C_9$, such as $C_1-C_6$) acids and alcohols ,or aromatic acids and alcohols, which are conventional in the field of pharmaceuticals and which retain the pharmacological properties of the free form.

Terms employed herein have the following meanings: A halogen or halo refers to fluorine, chlorine, bromine or iodine. The term $(C_1-C_6)$alkyl as employed herein as such or as part of another group includes both straight and branched chain radicals of up to 6 carbon atoms, preferably of 1, 2, 3 or 4 carbon atoms. In CO—$(C_1-C_9)$alkyl, the alkyl moiety includes both straight and branched chain radicals of up to 9 carbon atoms, preferably of up to 6 carbon atoms, e.g. 1, 2, 3 or 4 carbon atoms. The term $(C_1-C_6)$alkoxy as such or as part of another group refers to —O$(C_1-C_6)$alkyl, wherein $(C_1-C_6)$alkyl is as defined above. The term $(C_2-C_6)$alkenyl includes both straight and branched chain radicals of up to 6 carbon atoms, preferably of 2, 3 or 4 carbon atoms, containing double bond(s), e.g. one double bond. The term halo-$(C_1-C_6)$alkyl refers to $(C_1-C_6)$alkyl radical, as defined above, that is substituted by one or more halo radicals as defined above, e.g. trifluoromethyl, difluoromethyl etc. The term $(C_1-C_6)$alkylene refers to a straight or branched, saturated hydrocarbon chain divalent radical, e.g. methylene, ethylene, propylene, butylene and the like. The term $(C_2-C_6)$ alkenylene refers to a straight or branched, unsaturated hydrocarbon chain divalent radical, wherein the unsaturation is present as one or more, e.g. one, double bond(s), e.g. vinylene, propenylene, butenylene etc. The term $(C_3-C_7)$ cycloalkyl refers to a monocyclic 3- to 7-membered saturated carbocyclic ring, i.e. cyclopropyl, cyclobutyl, cyclopentyl, cyclohexyl or cycloheptyl ring. The 5- or 6-membered heterocyclyl with one to four heteroatoms selected independently from N, O and S means a monocyclic, partially or fully saturated, or aromatic hetero ring system. Examples of such heterocyclyls include piperidinyl, piperazinyl, morpholinyl, pyrrolyl, tetrahydropyridyl, dihydropyridyl, pyridyl, pyrazinyl, pyrimidinyl, pyridatsinyl, thienyl, furyl, thiazolyl, oxadiazolyl, thiadiazolyl tetrazolyl etc., such as tetrazolyl, e.g. 5-tetrazolyl, thienyl or pyridyl.

In case of di$(C_1-C_6)$alkylamino, the $(C_1-C_6)$alkyl chains can be identical or different.

It is evident to a skilled person that in the compounds I', I, Ia or Ib the nature of the optional substituent(s) $R_9$ and the maximal possible number thereof in a ring $R_8$ depend on the nature of the ring $R_8$. E.g. the option =O as $R_9$ is possible only for $(C_3-C_7)$cycloalkyl or saturated or partially saturated heterocyclic rings as $R_8$, wherein a double bond can be formed between the ring atom of $R_8$ and the said oxygen atom.

The compounds of the invention can be prepared by a variety of synthetic routes analogously or according to the methods known in the literature using suitable starting materials.

In general, the compounds of formula I', I, Ia or Ib, wherein $R_4$ and $R_5$ form together =O (compound Ic), can be prepared e.g. analogously or according to scheme 1:

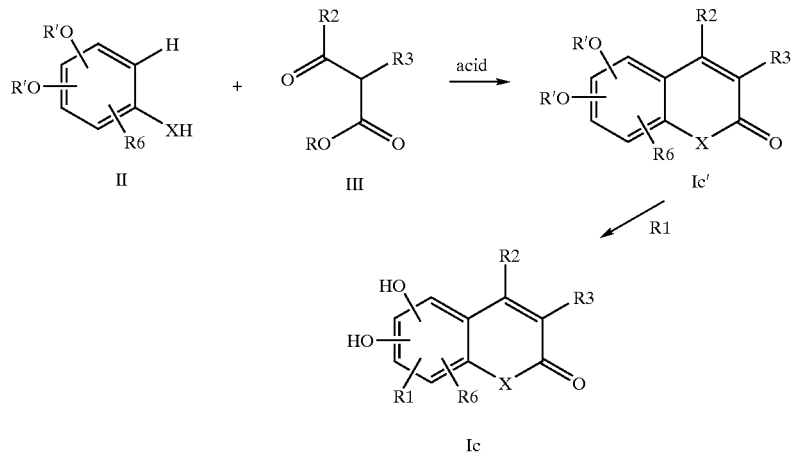

wherein X, $R_1$ to $R_3$ and $R_6$ are as defined above, each R' is independently H or a conventional protecting group for hydroxy, e.g. $(C_1-C_6)$alkyl, and R is $(C_1-C_6)$alkyl, e.g. methyl or ethyl.

Accordingly, reaction of scheme 1 corresponds to the known von Pechman reaction. A compound II is reacted with a compound III in acidic reaction conditions, e.g. in HCl/alcohol or 75% $H_2SO_4$, in a temperature between 0° C. and a room temperature, to obtain a compound Ic' which is then deprotected and a substituent $R_1$, e.g. $NO_2$, is introduced in a conventional manner to obtain a compound Ic.

The compounds I', I, Ia or Ib, wherein $R_4$ and $R_5$ form together =O (compound Ic), can further be prepared e.g. analogously or according to scheme 2:

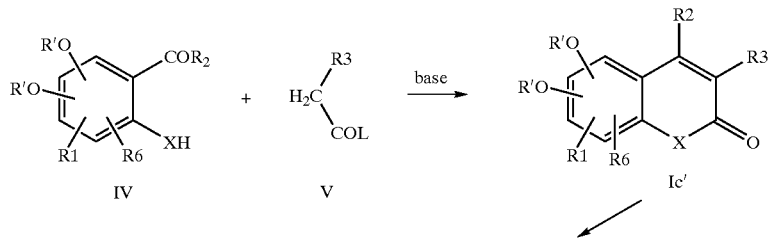

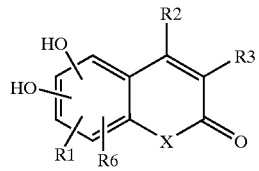

Ic wherein X, $R_1$ to $R_3$ and $R_6$ are as defined above, each R' is independently H or a conventional protecting group for hydroxy, e.g. $(C_1-C_6)$alkyl, and L is a conventional leaving group, e.g. OH, O—$(C_1-C_6)$alkyl or halogen.

The reaction of scheme 2 is analogous to the known Knövenagel-condensation. In general, a compound IV is condensed in a suitable solvent, e.g. an alcohol, DMF, an alcoholic DMF, or THF, with a compound V in the presence of a base, e.g. an inorganic fluoride compound or an organic amine, such as piperidine, at an elevated temperature to obtain a compound Ic' which is deprotected to compound Ic as defined above.

More specifically, e.g. compounds I', I, Ia or Ib, wherein $R_4$ and $R_5$ form together =O, $R_2$ is H and $R_3$ is —$(B)_m$—COOH, (compound Id), can also be prepared e.g. analogously or according to scheme 3:

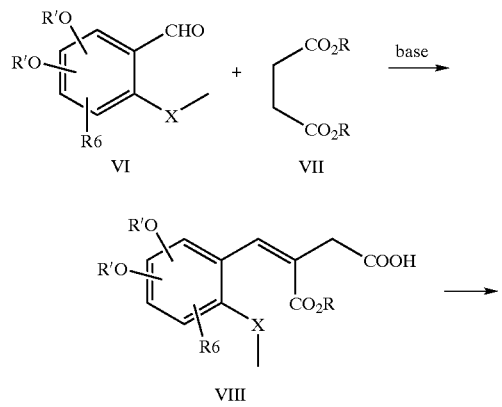

wherein X and $R_1$ and $R_6$ are as defined above, each R' is independently H or a conventional protecting group for hydroxy, e.g. $(C_1-C_6)$alkyl, and R is $(C_1-C_6)$alkyl, e.g. methyl or ethyl.

The reaction of scheme 3 is analogous to the known Stobbe condensation. Accordingly, a compound VI is reacted with a compound VII in a suitable solvent, e.g. an alcohol, in the presence of a strong base, such as $(C_1-C_6)$ alkyl-OMe, wherein Me is a metal ion, e.g. an alkaline metal ion, such as Na, in an elevated temperature to obtain a compound VIII. The compound VII is cyclized and demethylated in a manner known in the art using a known demethylation reagent, e.g. borontribromide, at a cooled temperature, e.g. (−20)° C., and then $R_1$, e.g. a nitro group, is introduced in a conventional manner to the resulted compound Id' to obtain compound Id as defined above.

A further method for preparing compounds I, wherein $R_4$ and $R_5$ form together =O, $R_1$ is $NO_2$ and X is $NR_7$, wherein $R_7$ is as defined above, (compound Ie) is illustrated in scheme 4:

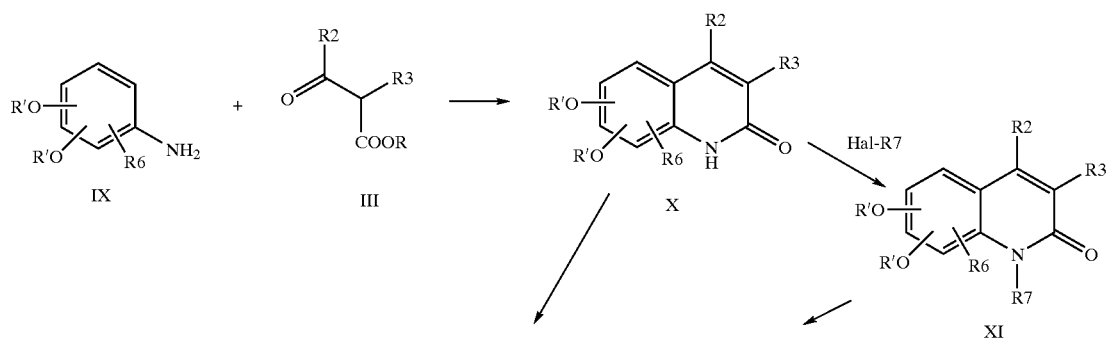

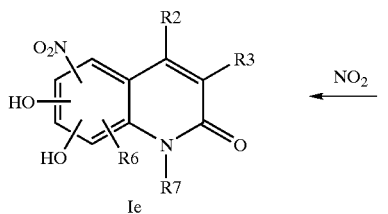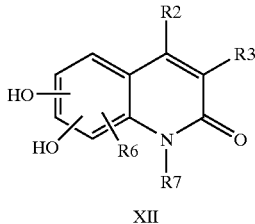

wherein $R_2$, $R_3$ and $R_6$ are as defined above, R' is a conventional protecting group for hydroxy, e.g. ($C_1$–$C_6$) alkyl, and R is ($C_1$–$C_6$)alkyl.

Accordingly, compound IX is reacted with compound III, in the presence or absence of a suitable solvent, at elevated temperature, e.g. at about 160° C., at a period of time. Then, preferably without the isolation of the reaction product, an acid is added to the reaction mixture at a temperature of 50–100° C. to obtain compound X which is optionally alkylated in the next step with Hal-$R_7$, wherein Hal is halogen and $R_7$ is ($C_1$–$C_6$)alkyl. The compound X ,or optionally XI, is deprotected, e.g. demethylated, and then nitrated in a conventional manner to obtain the end compound Ie as defined above.

Compounds I, wherein $R_4$ and $R_5$ are both ($C_1$–$C_6$)alkyl, e.g. methyl, and X is O, (compound If) can be prepared e.g. analogously or according to the method described by Cook et al. in J.Org.Chem., vol.30, 1965, p.4114, illustrated in scheme 5:

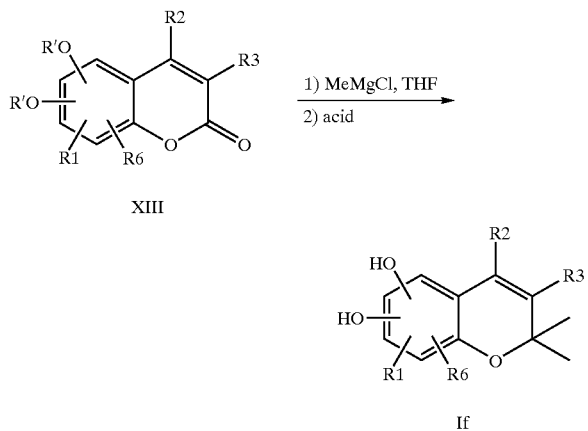

wherein $R_1$ to $R_3$ and $R_6$ are as defined above and R' is a conventional protecting group for hydroxy, e.g. $Me_3Si$.

Thus, compound XIII is reacted with MeMgCl in a suitable solvent, e.g. THF, and then deprotected with an acid to obtain the end compound If as defined above.

The starting materials II, III, IV, V, VI, VII, IX and XIII are commercially available or can be prepared via a variety of known synthetic routes known in the literature or described above.

It is obvious to a skilled person that, in the above reactions, any starting material or intermediate can be protected, if necessary, in a manner well known in the chemical field. Any protected functionality is subsequently deprotected in a usual manner.

Furthermore, in the above reaction schemes a substituent $R_1$ to $R_6$ and/or $R_7$ in the intermediates and/or end compounds of the invention may further be converted to another functionality of the invention, if desired, in a manner known to a skilled person.

It should be noted that the above described synthetic routes are meant to illustrate the preparation of the compounds of the invention and the preparation is by no means limited thereto, i.e. other synthetic methods which are within the general knowledge of a skilled person are also possible.

The compounds of the invention may be converted, if desired, into their pharmaceutically acceptable salt or ester form using methods well known in the art.

As already mentioned hereinbefore, the compounds of the invention show interesting pharmacological properties, namely they exhibit catechol-O-methyltransferase (COMT) enzyme inhibiting activity. The said activity of the compounds of the invention is demonstrated with the pharmacological tests presented below.

Experiment I: Determination of COMT Activity ($IC_{50}$)

The determination of $IC_{50}$ was performed by mesuring the COMT activity in a test sample which contained S-COMT enzyme (about 30 nM), 3 mM dopamine (as the substrate of COMT), 5 mM magnesium chloride, 0.05 mM S-adenosyl-L-methionine (AdoMet) and a test compound of the invention at various concentrations in 0.1 M phosphate buffer, pH 7.4, at 37° C.

The reaction in the test sample was initiated by adding the dopamine substrate to the sample mixture and, after incubation for 15 min at 37° C., the reaction was stopped with 4 M perchloric acid and stabilized further 10 min in ice bath. Thereafter the precipitated proteins were removed by centrifugation (4000×G for 10 min). The activity of COMT enzyme was measured by determining the concentration of the reaction products, 3-methyldopamine and 4-methyidopamine, by HPLC. The results were calibrated with 3-methyidopamine standards. See also T.Lotta et al., Biochemistry, vol.34(13), 1995, p.4204, T.Lotta et al. The $IC_{50}$ value is the concentration of the test compound which causes a 50% decrease in COMT activity. The results are shown in table 1.

TABLE 1

| The compound of example no. | IC50 (nM) |
|---|---|
| Example 6(b) | 30 |
| Example 7 | 30 |
| Example 8 | 50 |
| Example 9(c) | 20 |
| Example 10(d) | 35 |
| Example 11(c) | 10 |
| Example 12(b) | 10 |
| Example 13(c) | 60 |

Particularly, the compounds of the invention have preferable properties as therapeuticals. They can be used for the treatment of diseases or conditions wherein COMT inhibitors are indicated to be useful, i.a. in the treatment of Parkinson's disease for the potentiation of levodopa (+DDC) therapy.

The compounds of the invention may be administered enterally, topically or parenterally.

The compounds of the invention may be formulated alone or together with one or more active agents and/or together with a pharmaceutically acceptable excipient in different pharmaceutical unit dosage forms, e.g. tablets, capsules, solutions, emulsions and powders etc., depending on the route of administration, using conventional techniques. The pharmaceutically acceptable excipient can be selected from those conventionally used in the field of pharmaceuticals noticing the chosen route of administration.

The amount of the active ingredient varies from 0.01 to 100 weight-% depending on i.a. the type of the dosage form.

The specific dose level of the compounds of the invention depends, of course, on several factors such as the compound to be administered, the species, age and the sex of the subject to be treated, the condition to be treated and on the route and method of administration. For example, the compounds of the invention may administered from 0.5 $\mu$g/kg to 100 mg/kg per day for an adult male.

The present invention also provides a compound of the invention or an ester or salt thereof for use in a method of treatment of human or animal body.

The present invention further provides a compound of the invention or an ester or salt thereof, as well as a pharmaceutical composition thereof, for use as a COMT inhibitor, i.a. for the treatment of diseases and conditions where inhibition of COMT enzyme is useful, e.g. for the treatment of Parkinson's disease. The use of the compounds of the invention for the manufacture of a medicament to be used for the above indications is also provided. The invention further relates to a method for the treatment of above indicated conditions or diseases, by administering to a subject in need of such treatment an effective amount of the compound of the invention or a pharmaceutically acceptable ester or salt thereof.

The present invention will be explained in more detail by the following examples. The examples are meant only for illustrating purposes and does not limit the scope of the invention which is defined in claims.

PREPARATION EXAMPLE 1

(1a) 2-Hydroxy-3,4-dimethoxy-5-nitro-benzaldehyde

To a solution of 3,4-dimethoxy-2-hydroxybenzaldehyde (0.5 g) in acetic acid (10 ml) was added fuming nitric acid (0.12 ml). The reaction mixture was poured into ice water, the product extracted into ethyl acetate, washed with water, dried and evaporated. The product was triturated with water and filtered. Yield: 0.15 g.

NMR (90 MHz): 3.82 (s, 3H, CH$_3$O), 4.00 (s, 3H, CH$_3$O), 8.02 (s, 1H, ArH), 10.20 (s, 1H, CHO).

EXAMPLE 1

(a) 7,8-Dimethoxy-6-nitro-3-(4-nitro-phenyl)-chromen-2-one

A solution of 2-hydroxy-3,4-dimethoxy-5-nitro-benzaldehyde obtained from Preparation Example (1a) (0.46 g), 4-nitrophenyl acetic acid (0.39 g) and triethylamine (0.84 ml) in 1,2-dichloroethane (30 ml) was treated with phenyl dichlorophosphate (0.44 ml) at 0° C. The mixture was refluxed for 5 hours and cooled. The cool reaction mixture was diluted with methylene chloride, washed successively with 2.5 M NaOH, 2 M HCl and water, dried and evaporated. The product was finally triturated with pethroleum ether and filtered. Yield: 0.52 g, melting point 219–223° C.

NMR (90 MHz): 4.08 (s, 3H, CH$_3$O), 4.10 (s, 3H, CH$_3$O), 7.98–8.5 (m, 6 H).

(b) 7,8-Dihydroxy-6-nitro-3-(4-nitro-phenyl)-chromen-2-one

The product from the previous step (a) (0.5 g) was refluxed in concentrated hydrogen bromide (10 ml) under nitrogen for 5 hours. The product was worked up in the usual way and recrystallized from methanol. Yield: 0.18 g, melting point 270–280° C. NMR (90 MHz): 7.92–8.04 (m, 3H), 8.2–8.45 (m, 3 H).

EXAMPLE 2

(a) 7,8-Dimethoxy-6-nitro-2-oxo-2H-chromene-3-carboxylic acid ethyl ester

A solution of 3,4-dimethoxy-2-hydroxy-5-nitrobenzaldehyde obtained from Preparation Example (1a) (0.46 g), diethylmalonate (0.61 ml) and piperidine (two drops) was refluxed overnight. The product crystallized on cooling. Yield: 0.30 g.

NMR (400 MHz): 1.32 (t, 3H, CH$_3$CH$_2$O, J=7.5 Hz), 4.00 (s, 3H, MeO), 4.08 (s, 3H, MeO), 4.32 (q, 2H, CH$_3$CH$_2$O, J=7.5 Hz), 8.35 (s, 1H, ArH), 8.77 (s, 1H, lactone-H).

(b) 7,8-Dihydroxy-6-nitro-2-oxo-2H-chromene-3-carboxylic acid

The product from the previous step (a) (0.25 g) was refluxed in 47% HBr (3 ml) under nitrogen for 6 hours, evaporated and treated with water. Yield: 0.11 g, melting point 287–295° C.

NMR (90 MHz): 8.15 (s, 1H, ArH), 8.74 (s, 1H, lactone-H), 9–12 (br, 3H).

EXAMPLE 3

(a) 7,8-Dimethoxy-6-nitro-3-phenyl-chromen-2-one

A mixture of 3,4-dimethoxy-2-hydroxy-5-nitrobenzaldehyde obtained from Preparation example (1a) (0.91 g), phenacetylchloride (1.1 ml) and potassium carbonate (2.0 g) was refluxed in dry acetone (40 ml) overnight. Acetone was evaporated, cold water added and filtered. Yield: 0.69 g.

NMR (90 MHz): 4.00 (s, 6H, 2×CH$_3$O), 7.35–7.8 (m, 5 H, Ph), 8.16 (s, 1H, ArH), 8.25 (s, 1H, lactone-H).

(b) 7,8-Dihydroxy-6-nitro-3-phenyl-chromen-2-one

The product from the previous step (a) (0.6 g) was refluxed in 47% HBr (6 ml) under nitrogen for 10 hours, poured into ice water and filtered. Yield: 0.38 g, melting point 217–223° C.

NMR (90 MHz): 7.32–7.8 (m, 5H, Ph), 7.98 (s, 1H, ArH), 8.23 (s, 1H, lactone-H).

EXAMPLE 4

(a) 3-(4-Chloro-phenyl)-7,8-dimethoxy-6-nitro-chromen-2-one

2-Hydroxy-3,4-dimethoxy-5-nitro-benzaldehyde (2.44 g), 4-chlorophenyl acetic acid (1.82 g), PhOPOCl$_2$ (1.6 ml) and triethylamine (4.5 ml) in 1,2-dichloroethane (125 ml) were refluxed for 5 hours as described in example 1(a). Yield: 2.40 g.

NMR (90 MHz): 4.00 (s, 3H, CH₃O), 4.02 (s, 3H, CH₃O), 7.4–0.7.7 (m, 4H Ph), 8.16 (s, 1H, ArH), 8.20 (s, 1H, lactone-H).

(b) 3-(4-Chloro-phenyl)-7,8-dihydroxy-6-nitro-chromen-2-one

A mixture of the product from the previous step (a) (2 g) and 47% hydrogen bromide (50 ml) was refluxed under nitrogen atmosphere for six hours. After the usual work-up the product was recrystallized from methanol. Yield: 0.85 g.

NMR (90 MHz): 7.4–7.7 (m, 4H, Ph), 7.98 (s, 1H, ArH), 8.10 (s, 1H, lactone-H), 8.2–10 (br, 2H, OH).

EXAMPLE 5

(a) 7,8-Dimethoxy-6-nitro-3-o-tolyl-chromen-2-one

A mixture of 2-methylphenyl acetic acid (0.60 g), 2-hydroxy-3,4dimethoxy-5-nitro-benzaldehyde (0.91 g), PhPOCl₂ (0.60 ml) and triethyl amine (1.7 ml) were reacted in 1,2-dichloroethane as described in example 4. Yield: 0.68 g.

NMR (90 MHz): 2.22 (s, 3H, CH₃), 4.03 (s, 3H, CH₃O), 4.05 (s, 3H, CH₃O), 7.2–7.4 (m, 4H, Ph), 8.07 (s, 1H, ArH), 8.20 (s, 1H, lactone-H).

(b) 7,8-Dihydroxy-6-nitro-3-o-tolyl-chromen-2one

The product from the previous step (a) (0.68 g) was refluxed in 47% HBr (10 ml) for 8 hours under nitrogen and worked up in the usual way, Trituration with boiling ether afforded the product. Yield: 0.24 g, melting point 236–241° C.

NMR (90 MHz): 2.20 (s, 3H, CH₃), 7.28–7.38 (m, 4H), 7.95 (s, 1H), 7.98 (s, 1H).

EXAMPLE 6

(a) 7-Hydroxy-6-methoxy-8-nitro-3-phenyl-chromen-2-one

To a solution of 7-hydroxy-6-methoxy-3-phenyl-chromen-2-one (1.34 g) in acetone (40 ml) was added nitric acid (0.22 ml in 5 ml of CH₂Cl₂) and the resulting mixture stirred for 20 minutes. After evaporation of the solvents the product was recrystallized from ethanol. Yield: 0.85 g.

NMR (400 MHz): 3.92 (s, 3H, MeO), 7.52–7.56 (m, 2H, Ph), 7.63 (s, 1H, ArH), 7.67–7.71(m, 1H, Ph), 7.90–7.92 (m, 2H, Ph), 8.37 (s, 1H, CH=C).

(b) 6,7-Dihydroxy-8-nitro-3-phenyl-chromen-2-one

The product from the previous step (a) (0.8 g) was reacted with boron tribromide (1.1 ml) in dichloromethane (25 ml) under nitrogen and in room temperature overnight. The reaction mixture was treated with water, extracted in ethyl acetate and finally recrystallized from -ethanol. Yield: 100 mg, melting point 195–210° C.

NMR (400 MHz): 7.28 (s, 1H, arH), 7.39–7.42 (m, 3H, Ph), 7.67–7.71 (m, 2H, Ph), 8.23 (s, 1H, CH=C), 10.7 (br, OH).

EXAMPLE 7

3-Benzoyl-6,7-dihydroxy-5-nitro-chromen-2-one

Nitric acid solution (1.6 ml, 2 M in CH₂Cl₂) was added to a solution of 3-benzoyl-6,7-dihydroxy-chromen-2-one (0.89 g) in ethyl acetate (50 ml) at −16–10° C. The solvent was evaporated and the product run through a silica column with toluene-ethyl acetate acetic acid (8:1:1) as the solvent. The product was crystallized from ether. Yield: 40 mg, melting point 94–96° C.

NMR (400 MHz): 7.02 (s, 1H, ArH), 7.53–7.55 (m, 2H, Ph), 7.69–7.70 (m, 1H, Ph), 7.87–7.88 (m, 2H, Ph), 8.03 (s, 1H, CH=C), 10–12 (br, 2H, 2×OH).

EXAMPLE 8

2,3-Dihydroxy- 1-nitro-7,8,9,10-tetrahydro-benzo[c] chromen-6-one

A solution of 5 M HNO₃ in H₂SO₄ (1 ml) was added to solution of acetic acid 3-acetoxy-6-oxo-7,8,9,10-tetrahydro-6H-benzo[c]chromen-2-yl ester (1.6 g) in concentrated sulfuric acid (20 ml) and stirred at room temperature for an hour. The mixture was treated with ice (150 g) and filtered. The product was purified by column chromatography on silica (10% methanol in dichloromethane). Yield: 50 mg, melting point 238–255° C.

NMR (400 MHz): 1.64 (m, 4H), 2.40 (m, 2H), 3.43 (m, 2H), 6.86 (s, 1H), 10.22 (s, 1H), 11.40 (s, 1H).

EXAMPLE 9

(a) 6,7-Dihydroxy-2-imino-2H-chromene-3-carboxylic acid ethyl ester

To a solution of 2,4,5-trihydroxybenzaldehyde (2.94 g) and ethyl cyanoacetate (1.62 g) in DMF (20 ml) were added 20 drops (Pasteur pipette) of piperidine and eight drops of acetic acid and the solution kept at 80° C. under nitrogen for two hours. The product was filtered and washed with DMF and ethyl ether. Yield: 2.00 g.

NMR (300 MHz): 1.31 (t, 3H, J=7 Hz, CH₂CH₃), 4.29 (q, 2H, J=7 Hz, CH₂CH₃), 6.18 (s, 1H, ArH), 6.77 (s, 1H, ArH), 8.12 (s, 1H, CH=C), 8.5 (br, 1H), 8.8 (br, 1H), 9.6 (br, 1H).

(b) 6,7-Dihydroxy-2-oxo-2H-chromene-3-carboxylic acid

The product from the previous step (a) was refluxed in 1 M hydrochloric acid for four hours, cooled and filtered., Yield: 97%.

¹H NMR (300 MHz, DMSO-d₆): 6.82 (s,1H, ArH), 7.22 (s, 1H, ArH), 8.68 (s 1H, CH=C—COOH), 9.38 (b, 1H, OH), 10.83 (b, 1H, OH), 12.8 (b,1H, COOH).

(c) 6,7-Dihydroxy-5-nitro-2-oxo-2H-chromene-3-carboxylic acid

The product from the previous step (b) (0.22 g) in concentrated sulfuric acid (6 ml) was treated with potassium nitrate (0.10 g) at (−10)° C., poured into ice water and filtered. Yield: 0.21 g, melting point over 300° C.

¹H NMR (300 MHz, DMSO-d₆): 6.97 (s,1H, ArH), 8.26 (s,1H, CH=C—COOH), 9–13 (br, 3H, 2×OH+COOH).

EXAMPLE 10

(a) 7-Hydroxy-6-methoxy-2-oxo-2H-chromene-3-carboxylic acid ethyl ester

A mixture of 2,4-dihydroxy-5-methoxybenzaldehyde (1.68 g) and diethyl malonate (1.76 g) in DMF (5 ml) was treated with a few drops of piperidine and acetic acid and kept at 80–95° C. overnight. The reaction mixture was poured into ice water, acidified and filtered. Yield: 2.2. g.

NMR (300 MHz): 1.30 (t, 3H, Et), 3.82 (s, 3H, MeO), 4.26 (q, 2H, Et), 6.79 (s, 1H, ArH), 7.44 (s, 1H, ArH), 8.65 (s, !H, lactone-H), 10.90 (s, 1H, OH).

(b) 7-Hydroxy-6-methoxy-8-nitro-2-oxo-2H-chromene-3-carboxylic acid ethyl ester A solution of 1 M nitric acid in acetic acid (4.1 ml) was added to a suspension of the product from the previous step (a) (1.06 g) in acetic acid (20 ml) at room temperature. The starting suspension was dissolved and the product crystallized out. It was filtered, washed with acetic acid and ethyl ether. Yield: 0.53 g.

NMR (300 MHz): 1.30 (t, 3H, Et), 3.91 (s, 3H, MeO), 4.27 (q, 2H, Et),7.69 (s, 1H, ArH), 8.72 (s, 1H, lactone-H).

(c) 7-Hydroxy-6-methoxy-8-nitro-2-oxo-2H-chromene-3-carboxylic acid

The product from the previous step (b) (0.5 g) was hydrolyzed be refluxing it in a mixture of 4 M HCl (25 ml) and acetic acid (15 ml) for 30 minutes. The reaction mixture was agitated in ice bath and filtered. Yield: 0.34 g.

$^1$H NMR (300 MHz, DMSO-$d_6$): 7.35 (s,1H, ArH), 8.72 (s, 1H, CH=C—COOH), 10.7 (b, 2H, 2×OH), 12–13 (b, 1H, COOH).

(d) 6,7-Dihydroxy-8-nitro-2-oxo-2H-chromene-3-carboxylic acid

The suspension of the product from the previous step (c) (0.3 g) in dichloromethane (30 ml) was treated with boron tribromide (1.05 ml) at −25° C. and kept then at room temperature for two days. The reaction mixture was treated with ice water and extracted with ethyl acetate. The product was recrystallized from a mixture of water and 2-propanol. Yield: 0.18 g.

NMR (400 MHz): 7.35 (s, 1H, ArH), 8.73 (s, 1H, lactone-H), 10.7 (br, 1–2H), 12–13 (br, 1H).

EXAMPLE 11

(a) 2-(2,4,5-Trimethoxy-benzylidene)-succinic acid 1-ethyl ester

A solution of 2,4,5-trimethoxybenzaldehyde (19.6 g), diethyl succinate (17.4. g) and potassium tert-butoxide (11.2 g) in ethanol (70 ml) was refluxed for four hours. Ethanol was evaporated, water (400 ml) added and the water solution washed with diethyl ether. The water phase was acidified and the product extracted into ether. Recrystallization from ether yielded an approximately 4:1 mixture of cis-trans isomers. Yield: 22 g.

NMR (400 MHz) for the major isomer: 1.24 (t, 3H, Et-CH$_3$), 3.65 (s, 2H, CH$_2$COOH), 3.65 (s, 3H, Meo), 3.84 (s, 3H, MeO), 4.02 (s, 3H, MeO), 4.19 (q, 2H, Et-CH$_2$), 6.75 (s, 1H, ArH), 6.91 (s, 1H, ArH), 7.79 (s, 1H, CH=C), 12.45 (s, 1H, COOH).

(b) (6,7-Dihydroxy-2-oxo-2H-chromen-3-yl)-acetic acid

Boron tribromide (3 ml) was added to a solution of 2-(2,4,5-trimethoxy-benzylidene)-succinic acid 1-ethyl ester obtained from the previous step (a) (4 g) in dichloromethane (40 ml) at −20° C. under nitrogen atmosphere. The reaction was kept on ice for an hour and then at room temperature for three days. After water treatment, filtering and trituration with warm 2-propanol the product was filtered. Yield: 1.1 g NMR (400 MHz): 3.39 (s, 2H, CH$_2$), 6.75 (s, 1H, ArH), 7.03 (s, 1H, ArH), 7.77 (s, 1H, CH=C), 9.38 (s, 1H, OH), 10.15 (s, 1H, OH), 12.15 (br, 1H, COOH).

(c) (6,7-Dihydroxy-5-nitro-2-oxo-2H-chromen-3-yl)-acetic acid

Potassium nitrate (0.21 g) was added in small doses to a solution of the product from the previous step (b) (0.46 g) in sulfuric acid at (−18)° C.–(−12)° C. The solution was then kept at 0° C. for an hour, poured in ice and filtered. The product was triturated with hot water and filtered at ambient temperature. Yield: 0.15 g, melting point over 350° C.

NMR (400 MHz): 3.51 (s, 2H, CH$_2$), 6.94 (s, 1H, ArH), 7.69 (s, 1H, CH=C), 10.5 (br, 1H, OH), 11.6 (br; 1H, OH), 12.47 (br, 1H, COOH).

EXAMPLE 12

(a) 6,7-Dihydroxy-3-(2H-tetrazol-5-yl)-chromen-2-one

A mixture of 2,4,5-trihydroxybenzaldehyde (1.23 g), (2H-tetrazol-5-yl)-acetic acid ethyl ester (1.25 g), piperidine (1.36 g) and acetic acid (0.06 g) in DMF (10 ml) was stirred at 90° C. under nitrogen for two hours. After ice water treatment and acidification to pH 2 the product was filtered and triturated with hot ethanol. Yield: 0.55 g.

NMR (400 MHz): 6.80 (s, 1H), 7.06 (s, 1H, ArH), 8.71 (s,1H, lactone-H), 10–11 (br, 3H).

(b) 6,7-Dihydroxy-5-nitro-3-(1H-tetrazol-5-yl)-chromen-2-one

Potassium nitrate (0.14 g) was added to a solution of the product from the previous step (a) (0.4 g) in sulfuric acid (10 ml) at −18° C.–−12° C. The reaction mixture was poured into ice water and filtered. The product was extracted in hot acetone, concentrated and filtered. Yield: 50 mg, melting point over 315° C.

NMR (400 MHz): 7.08 (s, 1H, ArH), 8.49 (s, 1H, CH=C), 10–12.2 (br, 3H, OH, CN$_4$H).

EXAMPLE 13

(a) (6,7-Dihydroxy-4-methyl-2-oxo-2H-chromen-3-yl)-acetic acid ethyl ester

To a solution of 1,2,4-trihydroxybenzene (2.5 g) in 75% sulfuric acid (30 ml) at 5–10° C. was added diethyl 2-acetyl glutarate (4.3 g). The mixture was stirred at ambient temperature overnight poured in ice and filtered. The product (4.2 g) was used as such in the following step (b).

(b) (6,7-Dihydroxy-4-methyl-2-oxo-2H-chromen-3-yl)-acetic acid

A solution of (6,7-dihydroxy4-methyl-2-oxo-2H-chromen-3-yl)-acetic acid ethyl ester obtained from the previous step (a) (4.2 g) in acetic acid (20 ml) and 6 N hydrochloric acid (50 ml) was refluxed for two hours, cooled and filtered. Yield: 2.3 g.

NMR (400 MHz): 2.28 (s, 3H, CH$_3$), 3.62 (s, 2H, CH$_2$COOH), 6.74 (s, 1H, ArH), 7.07 (s, 1H, ArH), 9.34 (s, 1H, OH), 10.19 (s, 1H, OH).

(c) (6,7-Dihydroxy-4-methyl-5-nitro-2-oxo-2H-chromen-3-yl)-acetic acid

To a solution of the product from the previous step (b) (2 g) in concentrated sulfuric acid (10 ml) at −15° C. was added potassium nitrate (1.02 g). The mixture was kept at 0° C. for an hour, treated with ice water and filtered. Yield: 0.41 g, melting point over 350° C.

NMR(400 MHz): 2.49 (s, 3H, CH$_3$), 3.57 (s, 2H, CH$_2$), 6.92 (s, 1H, ArH), 10.3 (br, 1H, OH), 11.6 (br, 1H, OH).

What is claimed is:

1. A compound of formula I

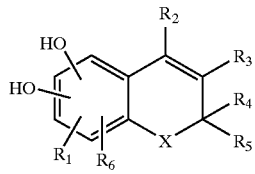

wherein the two OH— substituents in the phenyl moiety are in a position ortho to one another and $R_1$ in a position ortho to one of the hydroxy groups;

X is O or $NR_7$; wherein $R_7$ is H, $(C_1-C_6)$alkyl or —$(C_1-C_6)$alkyl-COOH;

$R_1$ is $NO_2$, CN, CHO, $CF_3$ or $(C_1-C_6)$alkyl-CO—;

$R_2$ and $R_3$ are each selected independently from H, OH, halogen, $NO_2$, SH, $NH_2$, $(C_1-C_6)$alkyl, $(C_2-C_6)$ alkenyl, $(C_1-C_6)$alkoxy, OH—$(C_1-C_6)$alkyl, halo-$(C_1-C_6)$alkyl, mono- or di$(C_1-C_6)$alkylamino, $SO_2R_{10}$, —CO—$(C_1-C_9)$alkyl, —$(Y)_n$—$(B)_m$—COOH and —$(Y)_n$—$(B)_m$—$R_8$; wherein m is 0 or 1;
n is 0 or 1;
Y is —CO— or —CHOH—;
B is $(C_1-C_6)$alkylene or $(C_2-C_6)$alkenylene;

$R_8$ is phenyl, naphthyl, $(C_3-C_7)$cycloalkyl or 5- or 6-membered heterocyclyl with one to four heteroatoms each selected independently from N, O and S, wherein the said phenyl, naphthyl, $(C_3-C_7)$cycloalkyl or 5- or 6-membered heterocyclyl is optionally substituted with one to five substituents $R_9$ each selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$ alkylamino-CO—, NHOH, CONHOH or $SO_2R_{10}$;

or $R_8$ is

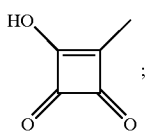

or $R_2$ and $R_3$ form together —$(CH_2)_r$—; wherein r is 3, 4 or 5;

$R_4$ and $R_5$ are independently H or $(C_1-C_6)$alkyl; or $R_4$ and $R_5$ form together =O, =S or =$NR_{11}$, wherein $R_{11}$ is H or $(C_1-C_6)$alkyl;

$R_6$ is H, $NO_2$, CN, CHO, halogen, $CF_3$ or $(C_1-C_6)$alkyl; and $R_{10}$ is $(C_1-C_6)$alkyl, $NH_2$, OH or mono- or di$(C_1-C_6)$ alkylamino;

with the provisos that (a) when X is O, $R_2$ is methyl, $R_3$ is H, $R_4$ and $R_5$ form together =O, $R_6$ is H and the two hydroxy substituents are at 7- and 8-positions, then $R_1$ is not CHO, (b) when X is O, $R_2$ is H or methyl, $R_3$ is H, $R_4$ and $R_5$ form together =O, $R_6$ is H and the two hydroxy substituents are at 6- and 7-positions, then $R_1$ is not 8-CO—$CH_3$, (c) when X is O, $R_2$ and $R_3$ are H, $R_4$ and $R_5$ are both methyl, $R_6$ is H and the two hydroxy substituents are at 7- and 8-positions, then $R_1$ is not —CO—$CH_3$, or pharmaceutically acceptable salts or pharmaceutically acceptable esters thereof.

2. A compound according to claim 1, which is a compound of formula Ia,

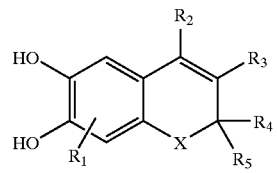

wherein X, $R_1$ to $R_5$ are as defined in claim 1, or pharmaceutically acceptable salt or pharmaceutically acceptable ester thereof.

3. A compound according to claim 1, which is a compound of formula Ib,

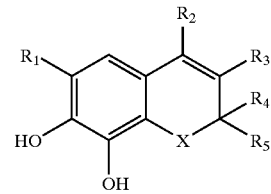

wherein X, $R_1$ to $R_5$ are as defined in claim 1, or pharmaceutically acceptable salt or pharmaceutically acceptable ester thereof.

4. A compound according to claim 1, wherein X is O.

5. A compound according to claim 1, wherein $R_1$ is $NO_2$, CN or $CF_3$.

6. A compound according to claim 1, wherein $R_4$ and $R_5$ form together =O.

7. A compound according to claim 1, wherein $R_3$ is —$(Y)_n$—$(B)_m$—COOH or —$(Y)_n$—$(B)_m$—$R_8$.

8. A compound according to claim 1, wherein $R_8$ is phenyl or $(C_3-C_7)$cycloalkyl, each unsubstituted or substituted with one or two substituent(s) $R_9$ each selected independently from OH, halogen, COOH, 5-tetrazolyl, $NO_2$ and $(C_1-C_6)$ alkyl or $R_8$ is 5-tetrazolyl.

9. A pharmaceutical composition comprising at least one compound according to claim 1 and a pharmaceutically acceptable excipient.

10. A pharmaceutical composition according to claim 9, wherein the two hydroxy substituents in the phenyl moiety are in 6- and 7-positions.

11. A pharmaceutical composition according to claim 9, wherein the two hydroxy substituents in the phenyl moiety are in 7- and 8-positions.

12. A method for the treatment of Parkinson's disease, said method comprising administering to a mammal in need of such treatment an effective amount of levodopa, and an effective amount of a compound of formula I',

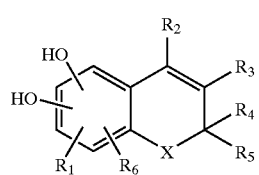

wherein the two OH— substituents in the phenyl moiety are in a position ortho to one another and R1 in a position ortho to one of the hydroxy groups;

X is O or $NR_7$; wherein $R_7$ is H, $(C_1-C_6)$alkyl or —$(C_1-C_6)$alkyl-COOH;

$R_1$ is $NO_2$, CN, CHO, $CF_3$ or $(C_1-C_6)$alkyl-CO—;

$R_2$ and $R_3$ are each selected independently from H, OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, mono- or di$(C_1-C_6)$alkylamino, $SO_2R_{10}$, —CO—$(C_1-C_9)$alkyl, —$(Y)_n$—$(B)_m$—COOH and —$(Y)_n$—$(B)_m$—$R_8$; wherein m is 0 or 1;

n is 0 or 1;

Y is —CO— or —CHOH—;

B is $(C_1-C_6)$alkylene or $(C_2-C_6)$alkenylene;

$R_8$ is phenyl, naphthyl, $(C_3-C_7)$cycloalkyl or 5- or 6-membered heterocyclyl with one to four heteroatoms each selected independently from N, O and S, wherein the said phenyl, naphthyl, $(C_3-C_7)$cycloalkyl or 5- or 6-membered heterocyclyl is optionally substituted with one to five substituents $R_9$ each selected independently from OH, halogen, COCH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH or $SO_2R_{10}$;

or $R_8$ is

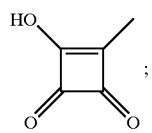

or $R_2$ and $R_3$ form together —$(CH_2)_r$; wherein r is 3, 4 or 5;

$R_4$ and $R_5$ are independently H or $(C_1-C_6)$alkyl; or $R_4$ and $R_5$ form together =O, =S or =$NR_{11}$, wherein $R_{11}$ is H or $(C_1-C_6)$alkyl;

$R_6$ is H, $NO_2$, CN, CHO, halogen, $CF_3$ or $(C_1-C_6)$alkyl; and $R_{10}$ is $(C_1-C_6)$alkyl, $NH_2$, OH or mono- or di$(C_1-C_6)$alkylamino;

or a pharmaceutically acceptable salt or pharmaceutically acceptable ester thereof, to potentiate the levodopa therapy.

13. A method according to claim 12, wherein the two hydroxy substituents in the phenyl moiety are in 6- and 7-positions.

14. A method according to claim 12, wherein the two hydroxy substituents in the phenyl moiety are in 7- and 8-positions.

15. A method according to claim 12, wherein a compound of formula I' is a compound of formula I

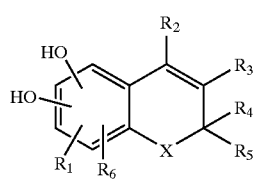

I wherein the two OH— substituents in the phenyl moiety are in a position ortho to one another and $R_1$ is in a position ortho to one of the hydroxy groups;

X is O or $NR_7$; wherein $R_7$ is H, $(C_1-C_6)$alkyl or —$(C_1-C_6)$alkyl-COOH;

$R_1$ is $NO_2$, CN, CHO, $CF_3$ or $(C_1-C_6)$alkyl-CO—;

$R_2$ and $R_3$ are each selected independently from H, OH, halogen, $NO_2$, SH, $NH_2$, $(C_1-C_6)$alkyl, $(C_2-C_6)$alkenyl, $(C_1-C_6)$alkoxy, OH—$(C_1-C_6)$alkyl, halo-$(C_1-C_6)$alkyl, mono- or di$(C_1-C_6)$alkylamino, $SO_2R_{10}$, —CO—$(C_1-C_9)$alkyl, —$(Y)_n$—$(B)_m$—COOH and —$(Y)_n$—$(B)_m$—$R_8$; wherein m is 0 or 1;

n is 0 or 1;

Y is —CO— or —CHOH—;

B is $(C_1-C_6)$alkylene or $(C_2-C_6)$alkenylene;

$R_8$ is phenyl, naphthyl, $(C_3-C_7)$cycloalkyl or 5- or 6-membered heterocyclyl with one to four heteroatoms each selected independently from N, O and S, wherein the said phenyl, naphthyl, $(C_3-C_7)$cycloalkyl or 5- or 6-membered heterocyclyl is optionally substituted with one to five substituents $R_9$ each selected independently from OH, halogen, COOH, 5-tetrazolyl, $NO_2$, SH, $NH_2$, CN, CHO, =O, $(C_1-C_6)$alkyl, $(C_1-C_6)$alkoxy, halo-$(C_1-C_6)$alkyl, mono- or di$(C_1-C_6)$alkylamino, CO—$(C_1-C_6)$alkyl, CO—$NH_2$, mono- or di$(C_1-C_6)$alkylamino-CO—, NHOH, CONHOH or $SO_2R_{10}$;

or $R_8$ is

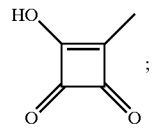

or $R_2$ and $R_3$ form together —$(CH_2)_r$—; wherein r is 3, 4 or 5;

$R_4$ and $R_5$ are independently H or $(C_1-C_6)$alkyl; or $R_4$ and $R_5$ form together =O, =S or =$NR_{11}$, wherein $R_{11}$ is H or $(C_1-C_6)$alkyl;

$R_6$ is H, $NO_2$, CN, CHO, halogen, $CF_3$ or $(C_1-C_6)$alkyl; and $R_{10}$ is $(C_1-C_6)$alkyl, $NH_2$, OH or mono- or di$(C_1-C_6)$alkylamino;

with the provisos that (a) when X is O, $R_2$ is methyl, $R_3$ is H, $R_4$ and $R_5$ form together =O, $R_6$ is H and the two hydroxy substituents are at the 7- and 8-positions, then $R_1$ is not CHO, (b) when X is O, $R_2$ is H or methyl, $R_3$ is H, $R_4$ and $R_5$ form together =O, $R_6$ is H and the two hydroxy substituents are at the 6- and 7-positions, then $R_1$ is not 8-CO—$CH_3$, (c) when X is O, $R_2$ and $R_3$ are H, $R_4$ and $R_5$ are both methyl, $R_6$ is H and the two hydroxy substituents are at the 7- and 8-positions, then $R_1$ is not —CO—$OH_3$ or a pharmaceutically acceptable salt or pharmaceutically acceptable ester thereof.

* * * * *

UNITED STATES PATENT AND TRADEMARK OFFICE
CERTIFICATE OF CORRECTION

PATENT NO.   : 6,951,870 B2
DATED        : October 4, 2005
INVENTOR(S)  : Jarmo Pystynen et al.

It is certified that error appears in the above-identified patent and that said Letters Patent is hereby corrected as shown below:

Column 21,
Line 38, "$R_8$" should read -- $R_6$ --.

Signed and Sealed this

Twenty-seventh Day of December, 2005

JON W. DUDAS
*Director of the United States Patent and Trademark Office*